United States Patent
Wang et al.

(10) Patent No.: US 11,382,629 B2
(45) Date of Patent: Jul. 12, 2022

(54) SURGICAL STAPLING DEVICE WITH AUDIBLE INDICATOR MECHANISM

(71) Applicant: Covidien LP, Mansfield, MA (US)

(72) Inventors: Zhaokai Wang, Shanghai (CN); Dongming Shen, Shanghai (CN); Xiliang Zhang, Shanghai (CN)

(73) Assignee: COVIDIEN LP, Mansfield, MA (US)

( * ) Notice: Subject to any disclaimer, the term of this patent is extended or adjusted under 35 U.S.C. 154(b) by 202 days.

(21) Appl. No.: 16/491,255

(22) PCT Filed: Mar. 9, 2017

(86) PCT No.: PCT/CN2017/076161
§ 371 (c)(1),
(2) Date: Sep. 5, 2019

(87) PCT Pub. No.: WO2018/161314
PCT Pub. Date: Sep. 13, 2018

(65) Prior Publication Data
US 2020/0029969 A1    Jan. 30, 2020

(51) Int. Cl.
*A61B 17/00* (2006.01)
*A61B 17/115* (2006.01)
(Continued)

(52) U.S. Cl.
CPC ........ *A61B 17/1155* (2013.01); *A61B 17/072* (2013.01); *A61B 2017/00115* (2013.01);
(Continued)

(58) Field of Classification Search
CPC ............... A61B 2017/00115; A61B 2090/0811
(Continued)

(56) References Cited

U.S. PATENT DOCUMENTS

| 3,193,165 A | 7/1965 | Akhalaya et al. |
| 3,388,847 A | 6/1968 | Kasulin et al. |

(Continued)

FOREIGN PATENT DOCUMENTS

| CA | 908529 A | 8/1972 |
| CA | 2805365 A1 | 8/2013 |

(Continued)

OTHER PUBLICATIONS

Extended European Search Report from Appl. No. 14181908.6 dated May 26, 2015.
(Continued)

*Primary Examiner* — Gloria R Weeks
(74) *Attorney, Agent, or Firm* — Carter, DeLuca & Farrell LLP

(57) ABSTRACT

A surgical stapling device includes a proximal handle assembly, an elongated central body portion that extends distally from the proximal handle assembly to a distal end portion, a tool assembly supported on the distal end portion of the elongated central body portion, and an audible indicator mechanism supported by the proximal handle assembly. The proximal handle assembly includes a contact arm and the audible indicator mechanism includes a cam member. The cam member contacts the contact arm of the proximal handle assembly as the cam member moves between distal and proximal positions to generate an audible sound that indicates that the tool assembly was fired.

15 Claims, 16 Drawing Sheets

(51) Int. Cl.
*A61B 17/072* (2006.01)
*A61B 90/00* (2016.01)

(52) U.S. Cl.
CPC ............ *A61B 2017/07257* (2013.01); *A61B 2090/0811* (2016.02)

(58) Field of Classification Search
USPC .................................................. 227/175.1
See application file for complete search history.

(56) References Cited

U.S. PATENT DOCUMENTS

| | | |
|---|---|---|
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |

(56) References Cited

U.S. PATENT DOCUMENTS

| | | |
|---|---|---|
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |

(56) References Cited

U.S. PATENT DOCUMENTS

| | | |
|---|---|---|
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 9,307,994 B2 | 4/2016 | Gresham et al. |
| 9,492,168 B2 | 11/2016 | Milliman |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0085015 A1* | 4/2006 | Whitfield ............... A61B 17/10 606/142 |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2007/0093856 A1 | 4/2007 | Whitfield et al. |
| 2007/0095877 A1 | 5/2007 | Racenet et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |

(56) References Cited

U.S. PATENT DOCUMENTS

| | | |
|---|---|---|
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2014/0276738 A1* | 9/2014 | Price ............... A61B 18/1445 606/33 |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0302792 A1 | 10/2016 | Motai |

FOREIGN PATENT DOCUMENTS

| | | |
|---|---|---|
| CN | 2461494 Y | 11/2001 |
| CN | 203506807 U | 4/2014 |
| CN | 104039242 A | 9/2014 |
| CN | 205041474 U | 2/2016 |
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 3187127 A2 | 7/2017 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |
| WO | 2017079970 A1 | 5/2017 |

OTHER PUBLICATIONS

European Examination Report from Appl. No. 14181908.6 dated May 3, 2016.

Extended European Search Report for application No. 17899332.5 dated Oct. 28, 2020.

Chinese Office Action for application No. 201780087867.7 dated Oct. 15, 2021 with English Translation.

* cited by examiner

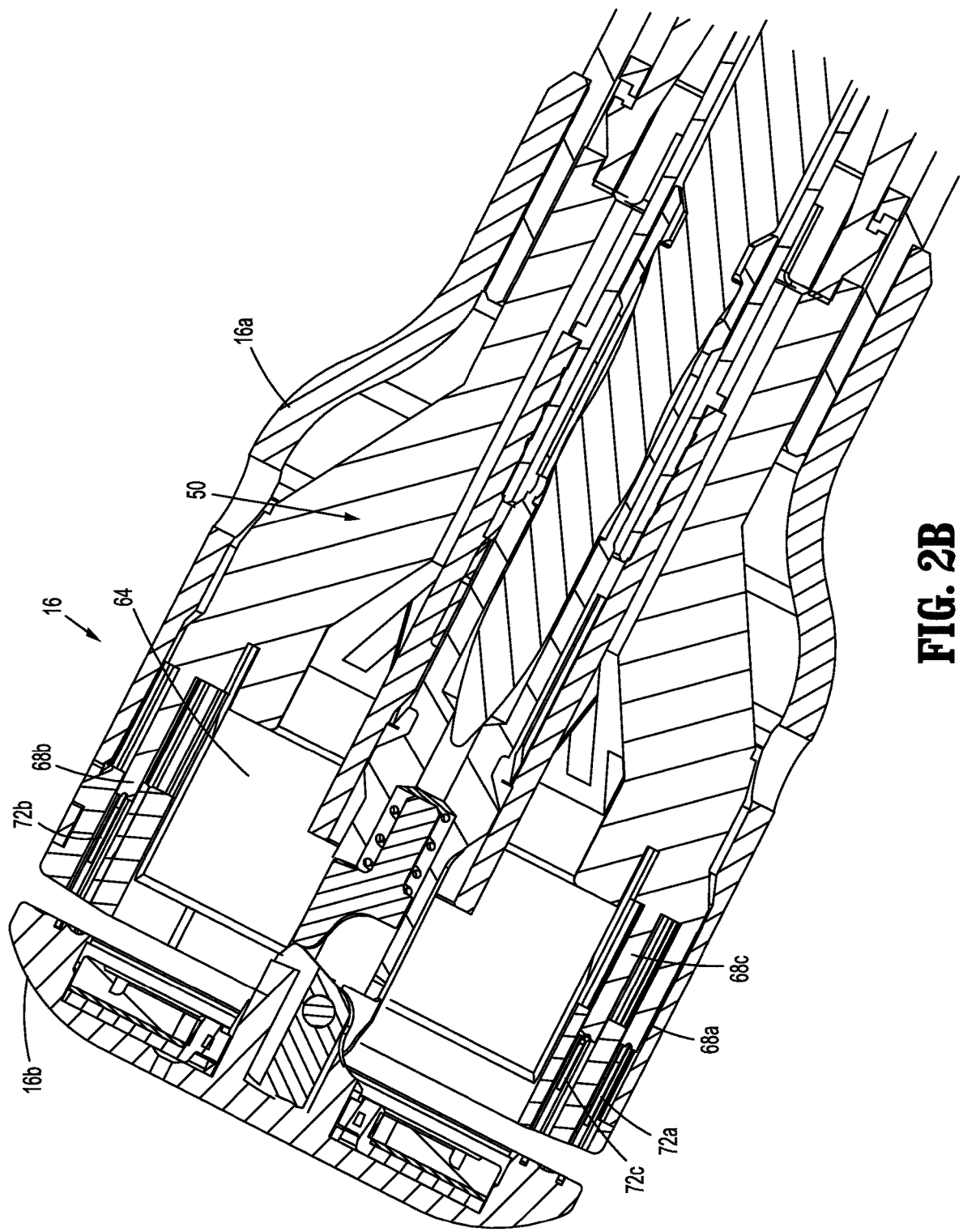

SURGICAL STAPLING DEVICE WITH AUDIBLE INDICATOR MECHANISM

CROSS-REFERENCE TO RELATED APPLICATIONS

This application is a U.S. National Stage Application filed under 35 U.S.C. § 371(a) which claims the benefit of and priority to International Patent Application Serial No. PCT/CN2017/076161, filed Mar. 9, 2017, the entire disclosure of which is incorporated by reference herein.

TECHNICAL FIELD

The present disclosure is directed to a surgical stapling device with an audible indicator mechanism and, more particularly, to a circular stapling device including an audible indicator mechanism that provides a notification to a clinician after firing is complete and after anvil tilt.

BACKGROUND

Surgical stapling devices are known to include visual, tactile and audible indicators that provide notice to a clinician that a certain event (or certain events) has taken place. For example, in circular stapling devices, it is known to provide an audible indication or notification to a clinician that firing of the stapling device is complete and that a tool assembly has been unapproximated a sufficient distance to allow an anvil head of the tool assembly to tilt to a low profile position (e.g., anvil tilt). In such devices, the audible indication may be faint or of a volume that may not be easily detected by the clinician.

A continuing need exists in the art for a surgical stapling device having an audible indicator mechanism that produces an audible indication that can be easily identified by clinician.

SUMMARY

According to one aspect of the present disclosure, a surgical stapling device is provided. The surgical stapling device includes a proximal handle assembly, an elongated central body portion that extends distally from the proximal handle assembly to a distal end portion, a tool assembly supported on the distal end portion of the elongated central body portion, and an audible indicator mechanism supported by the proximal handle assembly. The proximal handle assembly includes a contact arm and the audible indicator mechanism includes a cam member. The cam member is configured to contact the contact arm of the proximal handle assembly as the cam member moves between distal and proximal positions to generate an audible sound that indicates that the tool assembly was fired.

In some embodiments, the cam member may include a cam fin that is positioned to contact the contact arm of the proximal handle assembly to generate the audible sound. The contact arm may include an upper segment and a lower segment. The cam fin may be configured to contact one of the upper and lower segments to indicate that the distal tool assembly was fired.

In certain embodiments, the audible indicator mechanism may include a mounting body defining a cam channel. The cam member may include a cam pin that is slidably positioned within the cam channel to enable the cam member to move between the proximal and distal positions. The cam channel may include a plurality of legs. The cam pin may be receivable within each of legs as the cam member moves between the proximal and distal positions.

The mounting body may define an elongated channel that supports a spring. The spring may be coupled to a support bracket by a support pin. The spring may be a compression spring that urges the cam member into contact with the contact arm in response to tension in the compression spring. The spring may be coupled to the cam member by an elbow that extends from the cam member. The cam member may defines a central channel through which the support pin extends to enable the cam member to move vertically and axially relative to the support pin as the cam member moves between the proximal and distal positions.

In some embodiments, the distal tool assembly includes a circular anvil and a circular shell assembly that are positioned to move between unapproximated and approximated positions.

In certain embodiments, the cam member may be positioned to move from the distal position to the proximal position to generate the audible sound.

According to yet another aspect, an audible indicator mechanism for a surgical stapling device is provided. The audible indicator mechanism includes a mounting assembly, a spring assembly supported by the mounting assembly, a support bracket mounted to the mounting assembly, and a cam member coupled to the spring assembly and supported between the support bracket and the mounting assembly. The cam member is supported for movement between distal and proximal positions relative to the support bracket to generate an audible sound that indicates that the surgical stapling device was fired.

In some embodiments, the cam member may include a cam fin that is positioned to generate the audible sound as the cam member moves from the distal position to the proximal position.

In certain embodiments, the mounting assembly may include a mounting body that defines a cam channel. The cam member may include a cam pin that is slidably positioned within the cam channel to enable the cam member to move between the proximal and distal positions. The cam channel may include a plurality of legs. The cam pin may be receivable within each leg as the cam member moves between the proximal and distal positions.

The spring assembly may include a spring and the mounting body may define an elongated channel that supports the spring. The spring may be coupled to the support bracket by a support pin. The spring may be a compression spring that urges the cam member toward the proximal position in response to tension in the compression spring. The spring may be coupled to the cam member by an elbow that extends from the cam member.

In some embodiments, the cam member may define a central channel through which the support pin extends to enable the cam member to move vertically and axially relative to the support pin as the cam member moves between the proximal and distal positions.

The cam member may be positioned to move from the distal position to the proximal position to generate the audible sound.

Other aspects, features, and advantages will be apparent from the description, the drawings, and the claims that follow.

BRIEF DESCRIPTION OF THE DRAWINGS

Various embodiments of the presently disclosed surgical stapling devices are described herein below with reference to the drawings, wherein:

FIG. 2B is an enlarged view of the tool assembly of FIG. 2A showing the tool assembly in an approximated position;

DETAILED DESCRIPTION

Figure 1:
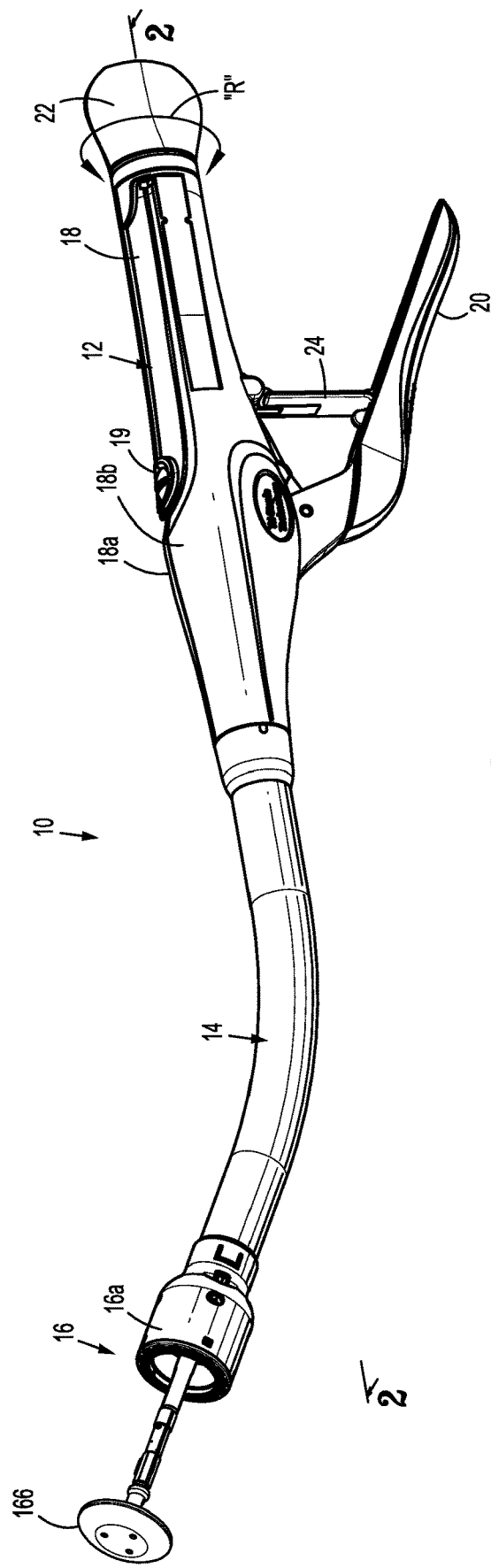
FIG. 1 is a perspective view of a surgical stapling device in accordance with the principles of the present disclosure.

The presently disclosed device will now be described in detail with reference to the drawings in which like reference numerals designate identical or corresponding elements in each of the several views. In this description, the term "proximal" is used generally to refer to that portion of the device that is closer to a clinician, while the term "distal" is used generally to refer to that portion of the device that is farther from the clinician. Further, directional terms such as upwardly, downwardly, laterally and the like are used simply for convenience of description and are not intended to limit this disclosure. In addition, the term "endoscopic" is used generally used to refer to endoscopic, laparoscopic, arthroscopic, and/or any other procedure conducted through small diameter incision or cannula. In addition, the term clinician is used generally to refer to medical personnel including doctors, nurses, and support personnel.

In the following description, well-known functions or constructions are not described in detail to avoid obscuring the present disclosure in unnecessary detail.

As seen in FIG. 1, a surgical stapling device 10 includes a proximal handle assembly 12, an elongated central body portion 14 that extends distally from the proximal handle assembly 12, and a distal tool assembly 16 supported on a distal end portion of the elongated central body portion 14. The distal tool assembly 16 includes a shell assembly 16a and an anvil assembly 16b that cooperate to fasten tissue together.

The handle assembly 12 of the surgical stapling device 10 includes a stationary handle 18, a firing trigger 20, and a rotatable approximation knob 22. The stationary handle 18 of the handle assembly 12 is formed from handle sections 18a and 18b, which, when secured together, define a housing for the internal components of the handle assembly 12. The handle assembly 12 further includes a pivotally mounted trigger lock 24 fastened to the handle sections 18a and 18b that is manually positioned to obstruct movement of the firing trigger 20 to prevent inadvertent firing of the stapling device 10. The stationary handle 18 includes a bulbous indicator 19 that is supported on an upper surface of the stationary handle 18 to provide an indication to the clinician when the shell assembly 16a and the anvil assembly 16b of the distal tool assembly 16 of the stapling device 10 are approximated and in a fire-ready position.

Approximation Mechanism

Figure 2:
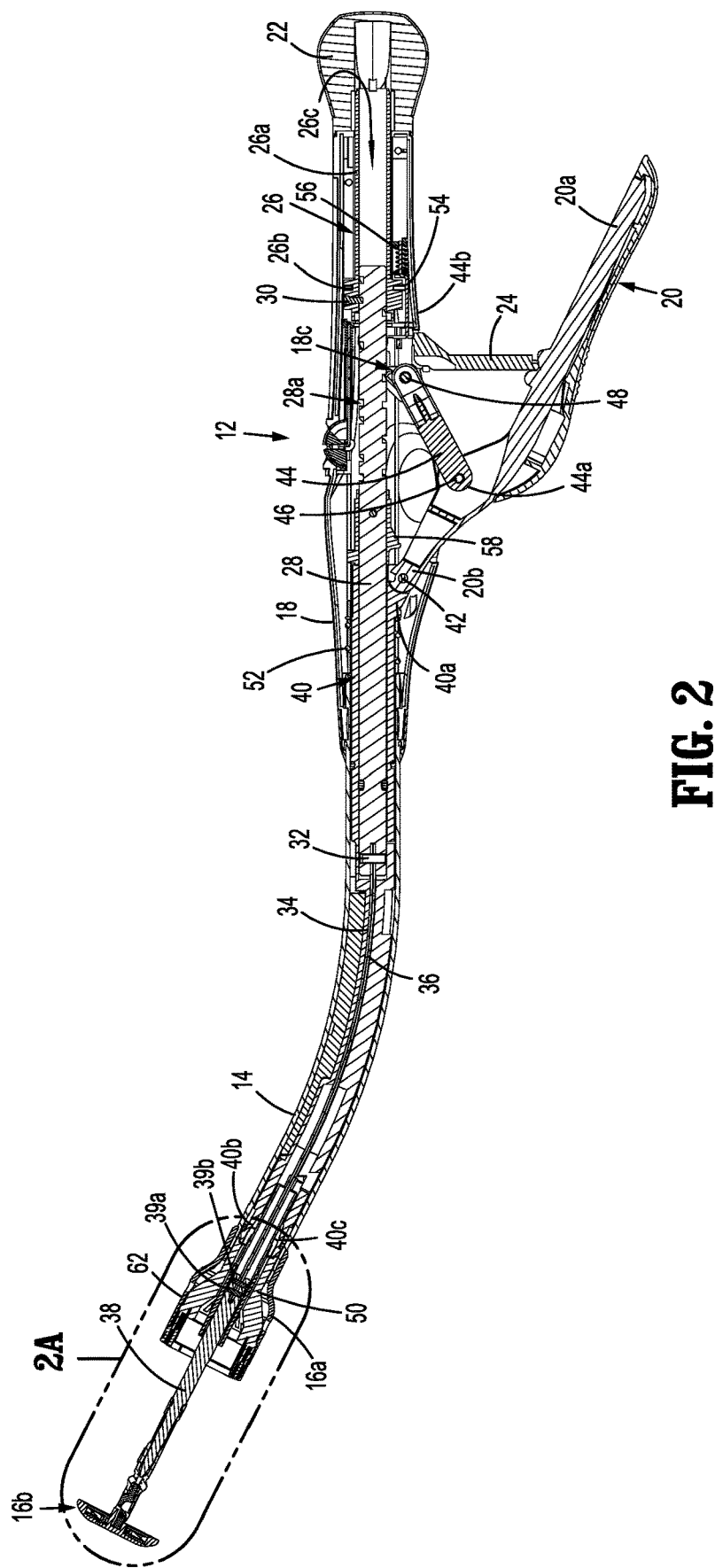
FIG. 2 is a cross-sectional view of the surgical stapling device of FIG. 1 as taken along section line 2-2 shown in FIG. 1.

With reference to FIG. 2, a distal end portion of the approximation knob 22 of the handle assembly 12 is rotatably fixed to a proximal end portion of a rotatable sleeve 26 such that rotation of the knob 22 causes concurrent rotation of the sleeve 26. The rotatable sleeve 26 extends distally from the approximation knob 22 and has a cylindrical hollow body portion 26a and a collar 26b that together define a central bore 26c. The central bore 26c of the rotatable sleeve 26 receives a drive screw 28 having an outer surface that defines a helical channel 28a. The helical channel 28a of the screw 28 receives a pin 30 that extends radially through the collar 26b of the sleeve 26. The rotatable sleeve 26 is axially fixed with respect to the stationary handle 18 via a flange/recess interconnection (not shown) such that rotation of the sleeve 26 about the screw 28 causes the pin 30 to move along the channel 28a of the screw 28 to effect axial movement of the screw 28 within the central bore 26c of the rotatable sleeve 26.

A distal portion of the drive screw 28 is secured to proximal end portions of screw extensions 34, 36 using, e.g., a pin 32. The screw extensions 34, 36 are flexible and extend distally through the central body portion 14 of the surgical stapling device 10 to an anvil retainer 38. The anvil retainer 38 has a proximal end portion that is secured to a distal portion of the screw extensions 34 and 36 using, e.g., pins 39a, 39b, and a distal end portion that is configured to be releasably coupled to the anvil assembly 16b of the distal tool assembly 16, whereby rotation of the knob 22 effectuates axial movement of the anvil assembly 16b relative to the shell assembly 16a of the distal tool assembly 16. The knob 22 can be rotated, as indicated by arrows "R" (FIG. 1) to selectively move the anvil assembly 16b relative to the shell assembly 16a, as indicated by arrow "Z" (FIG. 2A), between an unapproximated position (FIG. 2A) and an approximated position (FIG. 2B).

Firing Mechanism

Figure 3:
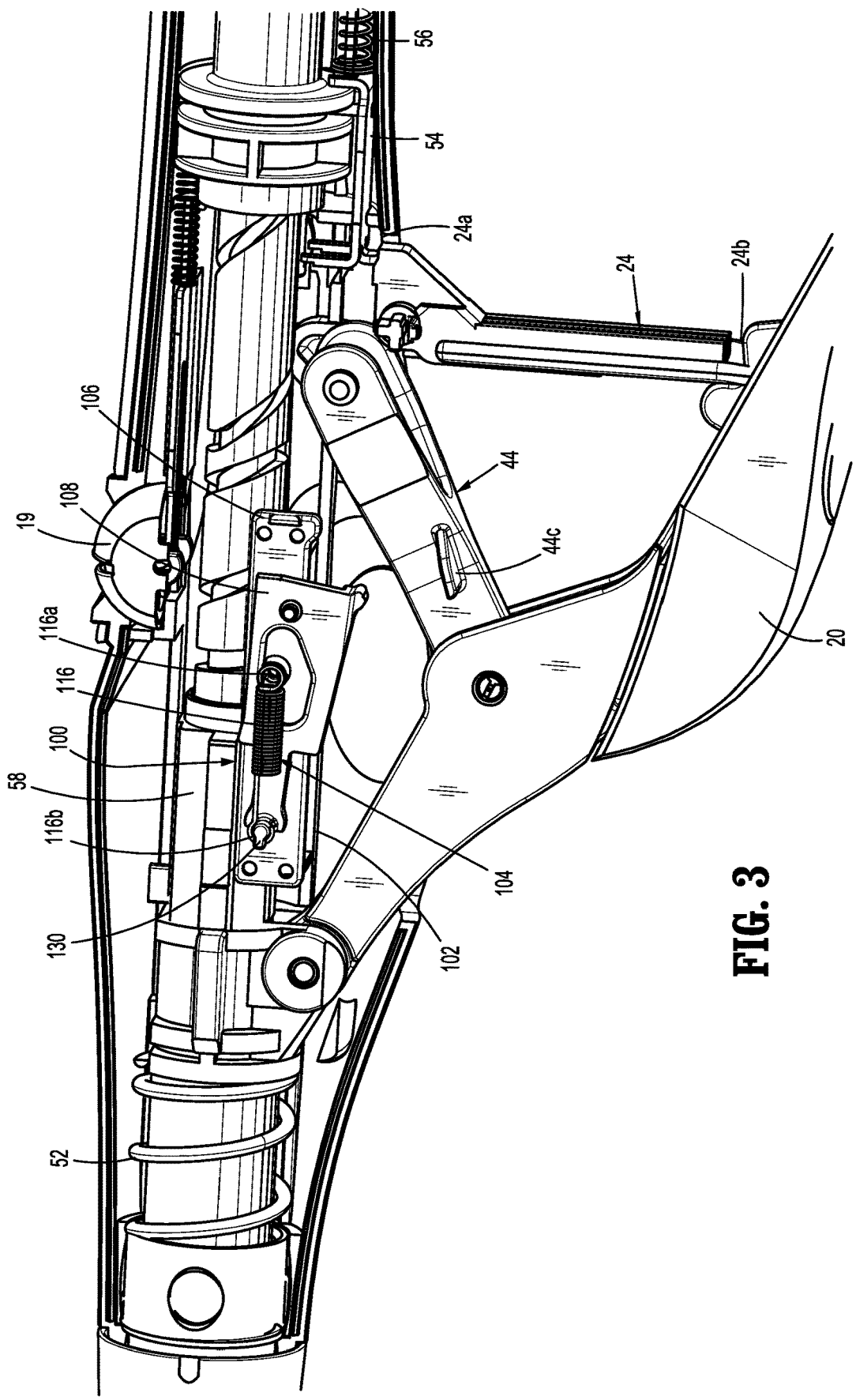
FIG. 3 is an enlarged perspective view of a portion of a handle assembly of the surgical stapling device of FIG. 1 with a handle section of the handle assembly removed.
Figure 4:
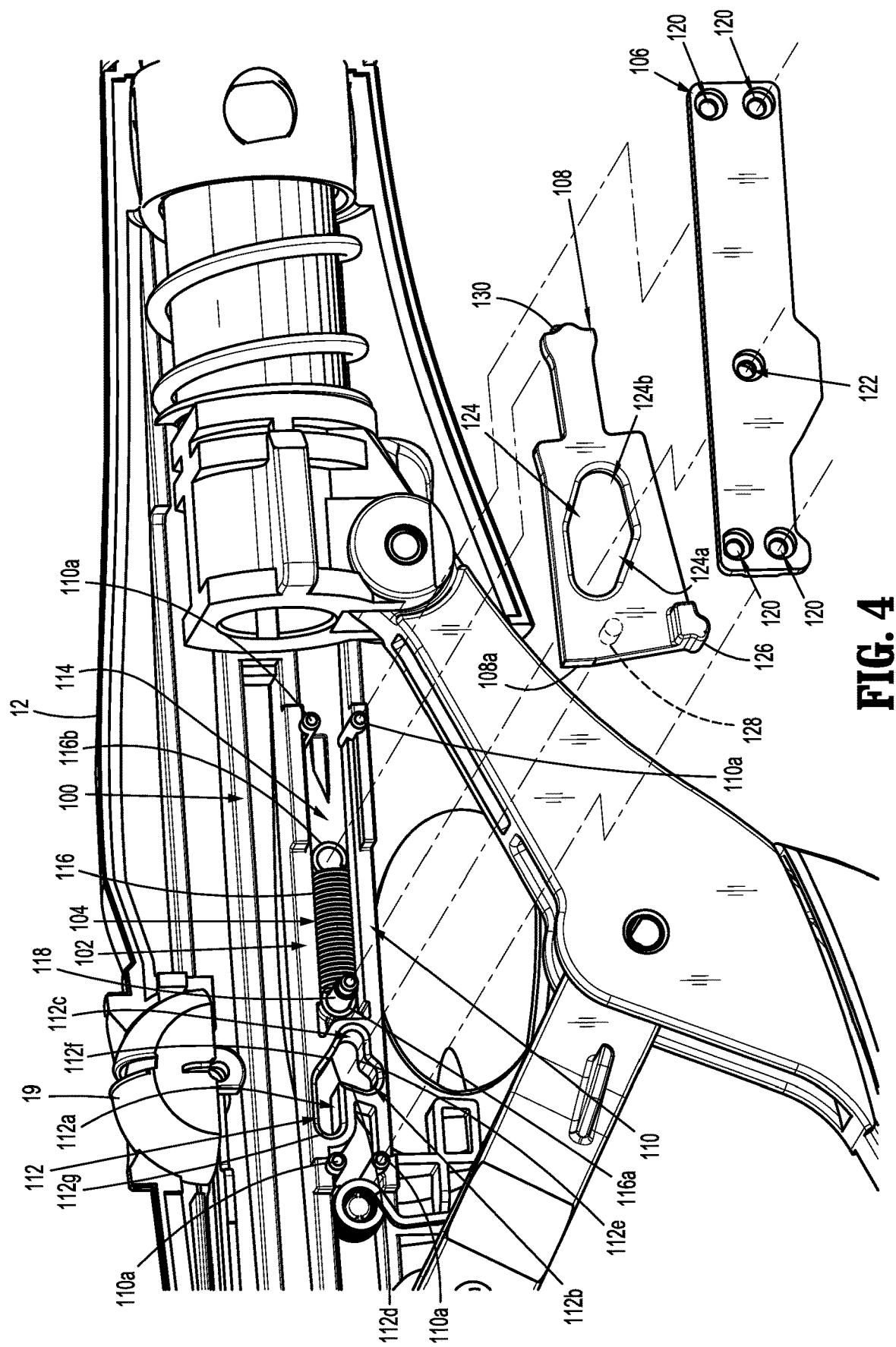
FIG. 4 is an enlarged perspective view of a portion of the handle assembly of the surgical stapling device of FIG. 1 with portions of an audible indicator mechanism of the handle assembly shown separated from the handle assembly.
Figure 5:
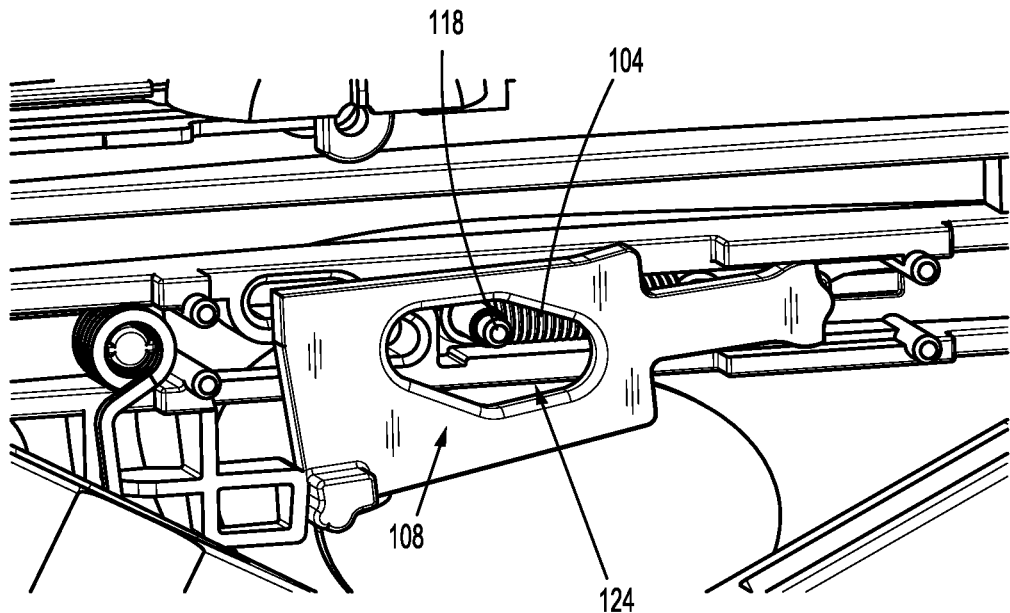
FIG. 5 is a perspective view illustrating a portion of the handle assembly shown in FIG. 3 showing a first side of the audible indicator mechanism of FIG. 4.

With continued reference to FIG. 2, the central body portion 14 of the surgical stapling device 10 supports an elongated pusher link 40. The elongated pusher link 40 has a proximal end portion that supports a coupling portion 40a and a distal end portion including resilient engagement fingers 40b, 40c. The fingers 40b, 40c of the elongated pusher link 40 are configured to lockingly engage with a proximal end portion of a pusher 50 of the shell assembly 16a. The firing trigger 20 of the handle assembly 12 has a proximal portion 20a and a distal portion 20b. The distal portion 20b of the firing trigger 20 is pivotally connected to the coupling portion 40a of the elongated pusher link 40 by a pivot member 42 to facilitate pivotal movement of the firing trigger 20 relative to the stationary handle 18 of the handle assembly 12. The firing trigger 20 of the handle assembly 12 is pivotally connected to a first end portion 44a of a firing link 44 by a pivot member 46. The firing link 44 includes a second end portion 44b that is pivotally secured to the stationary handle 18 by a pivot member 48 that is vertically movable within a slot 18c (FIG. 10) defined in the stationary handle 18. The firing link 44 further includes a wing member 44c (FIG. 3) that extends laterally from the firing link 44. The elongated pusher link 40 is slidably supported within the central body portion 14 of the surgical stapling device 10 about the drive screw 28 along the central body portion 14 between a retracted, nonfired position and an advanced, fired position. The elongated pusher link 40 supports a spring 52 (FIG. 3). The spring 52 is positioned about an outer surface of the elongated pusher link 40 between the stationary handle 18 and the coupling portion 40a of the elongated pusher link 40 to bias the elongated pusher link 40 proximally toward the retracted, non-fired position.

Trigger Lockout

Referring also to FIG. 3, the handle assembly 12 of the surgical stapling device 10 slidably supports a lockout member 54 (FIG. 2) within the handle assembly 12 between retracted and advanced positions. The lockout member 54 is biased by a coil spring 56 toward the advanced position to maintain the trigger lock 24 in a locked position to prevent actuation of the firing trigger 20 of the handle assembly 12. The drive screw 28 includes a screw stop 58 that is axially fixed thereon, and that is movable from an advanced position located adjacent to the elongated pusher link 40 to a retracted position located adjacent to the collar 26b of the rotatable sleeve 26 (FIG. 10) to control the degree of movement of the anvil assembly 1/6b of the distal tool assembly 16 in relation to the shell assembly 16a of the distal tool assembly 16 such as disclosed in U.S. Pat. Nos. 6,945,444, 9,307,994, and 9,492,168, the contents of each of which are incorporated by reference herein in their entirety.

Figure 13:
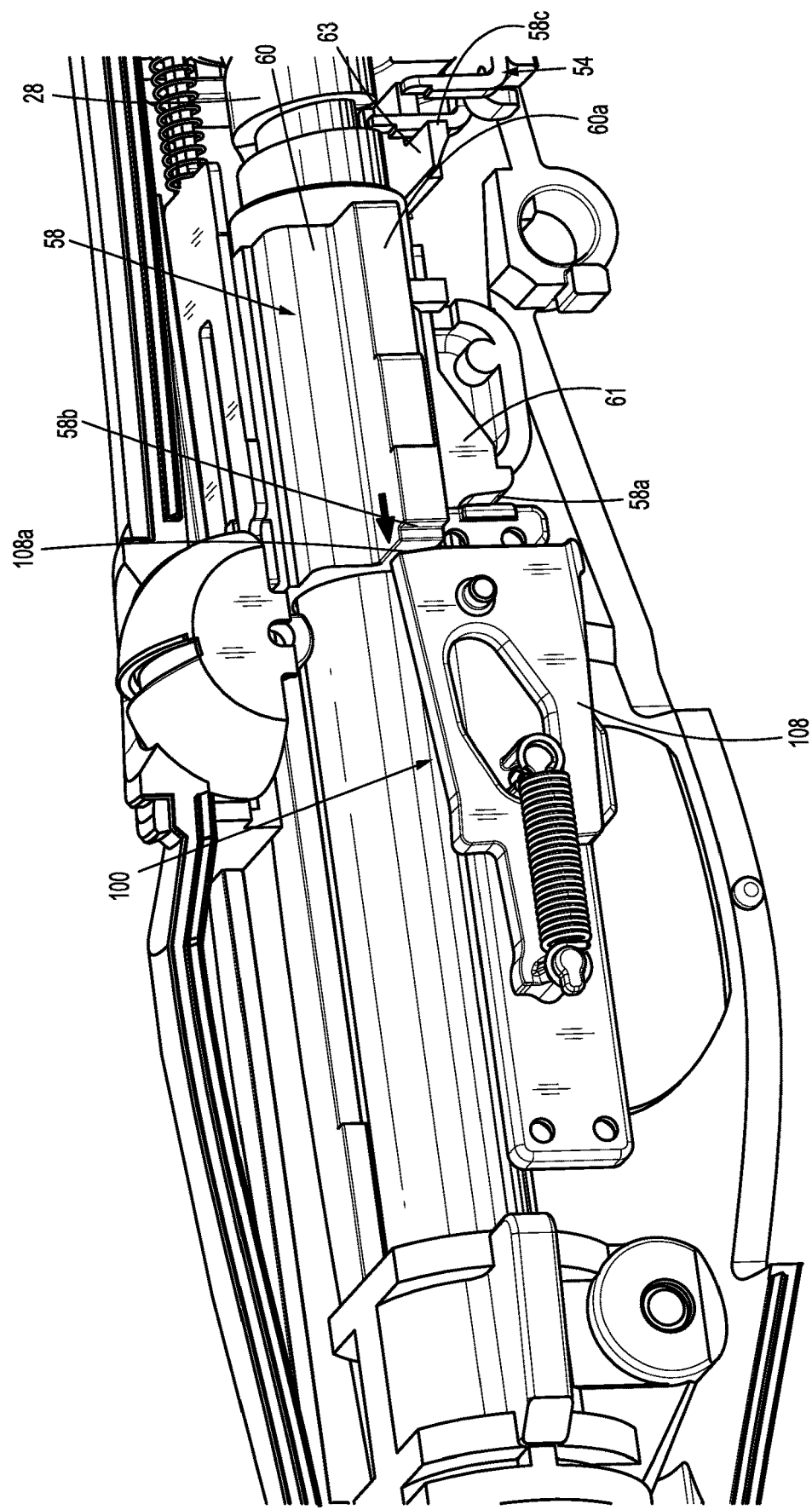
FIGS. 13-16 are progressive views illustrating operation of the audible indicator mechanism of FIG. 4 as the anvil and shell assemblies of the surgical stapling device of FIG. 1 are unapproximated.
Figure 14:
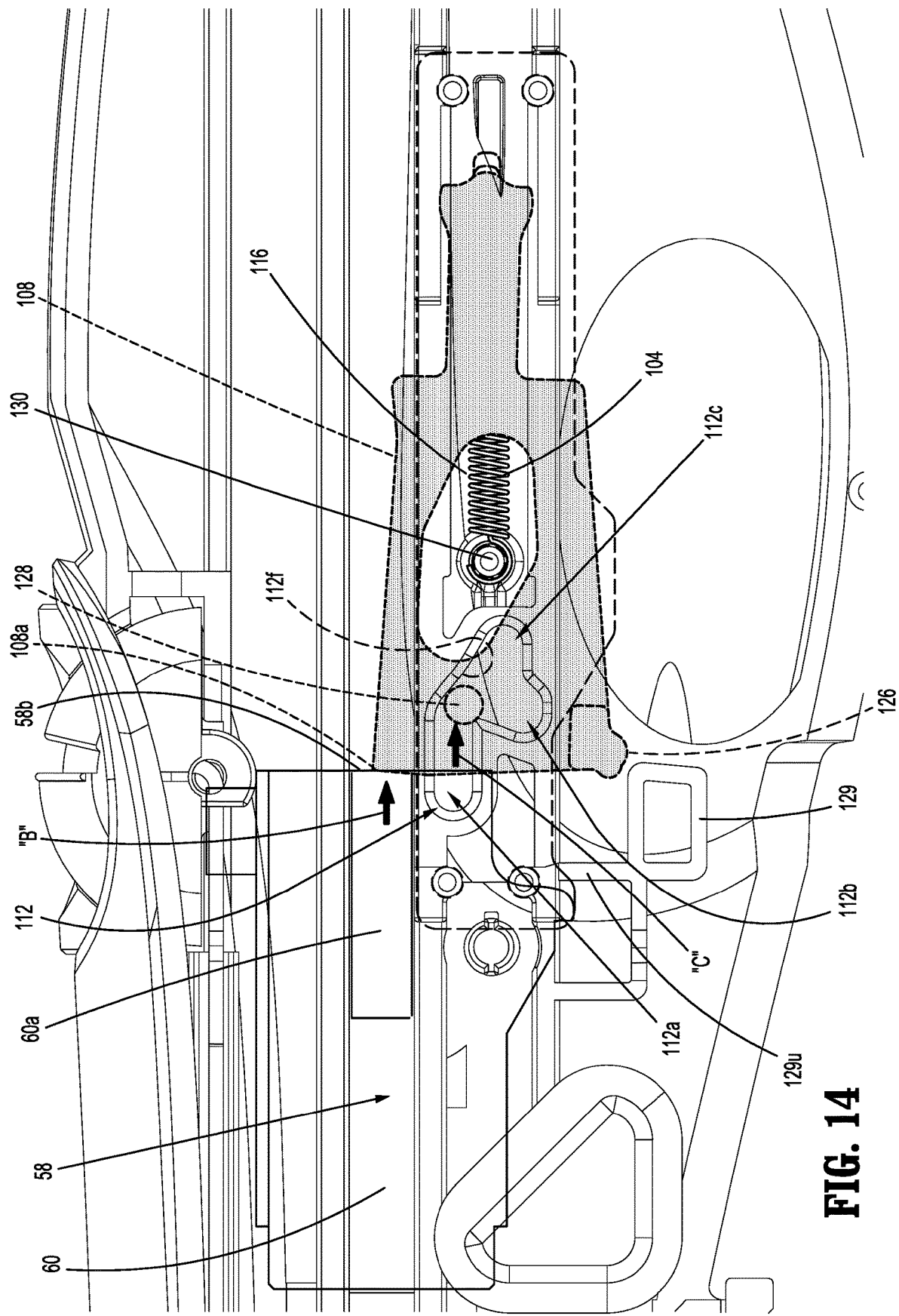
Figure 15:
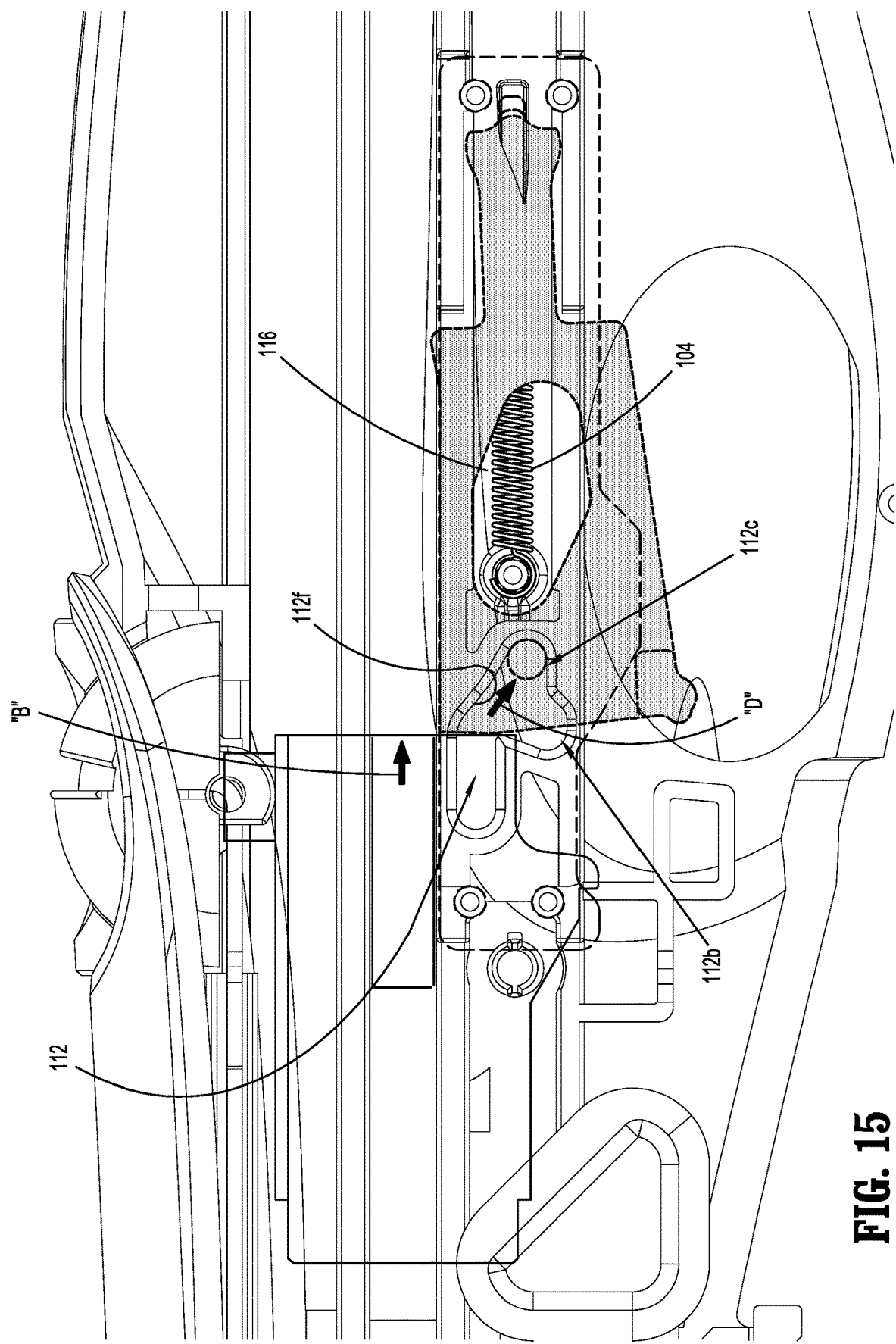
Figure 16:
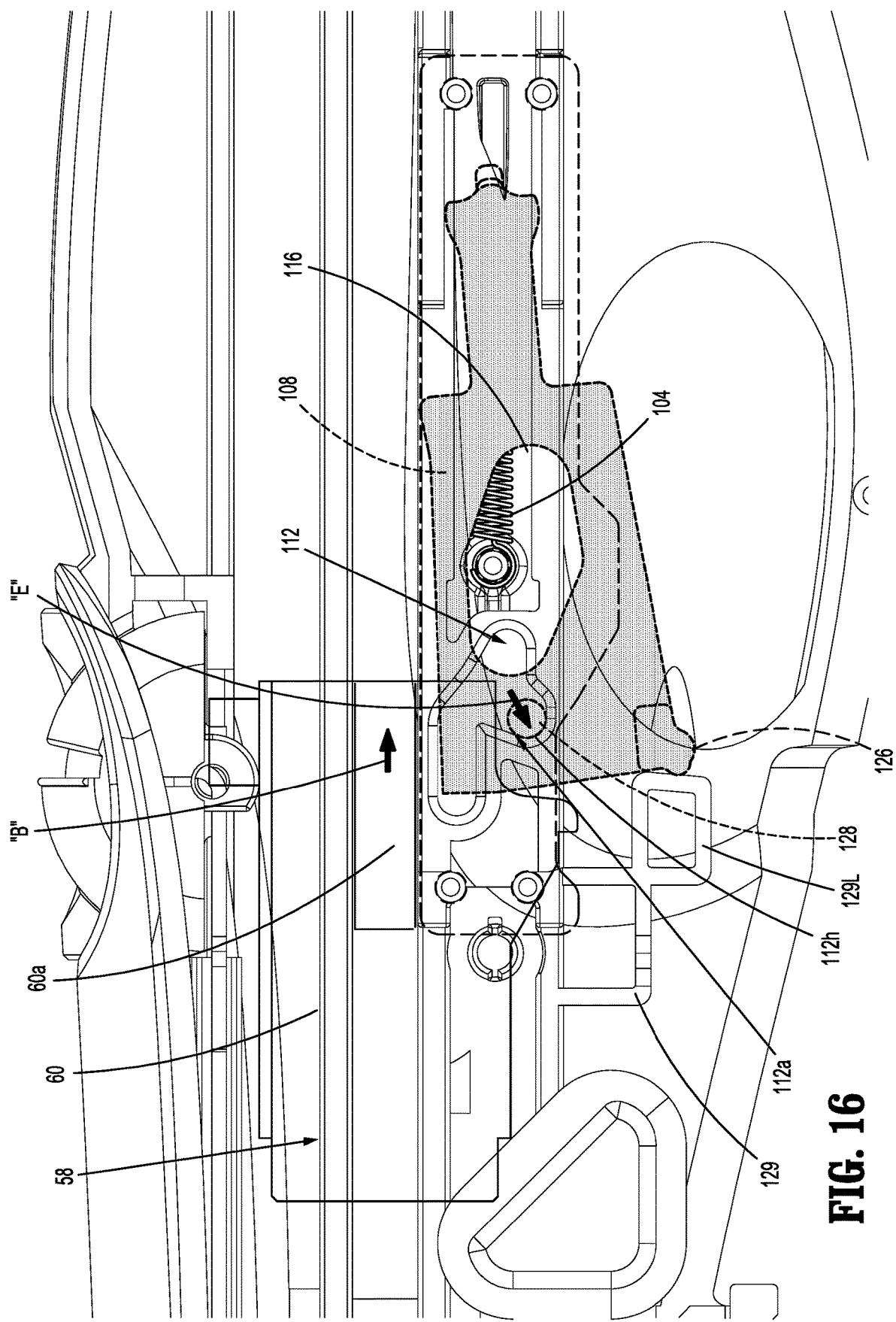

With reference also to FIG. 13, the screw stop 58 includes a body 60 having a wing 60a that extends laterally from the body 60 of the screw stop 58, a stem 61 that extends downwardly from a distal portion of the body 60 of the screw stop 58, and a tab 63 that extends laterally from a proximal portion of the body 60 of the screw stop 58. The stem 61 defines a first abutment surface 58a that is configured to engage the firing link 44, the wing 60a defines a second abutment surface 58b that is configured to engage an audible indicator mechanism 100, and the tab 63 defines a third abutment surface 58c configured to engage the lockout member 54.

Referring again to FIGS. 1 and 3, in order to unlock the firing trigger 20, the drive screw 28 and the screw stop 58 are drawn proximally by rotation of the approximation knob 22. During approximation of the shell assembly 16a and the anvil assembly 16b, the screw stop 58 moves proximally so that the third abutment surface 58c of the screw stop 58 contacts the lockout member 54 and drives the lockout member 54 proximally against the bias of (e.g., tension in) the coil spring 56. Proximal movement of the lockout member 54 separates the lockout member 54 from contact with an upper end portion 24a of the trigger lock 24 and enables a lower end portion 24b of the trigger lock 24 to pivot away from the firing trigger 20. Once the trigger lock 24 is pivoted away from the firing trigger 20, the firing trigger 20 can be actuated.

Shell Assembly

With reference to FIGS. 2-2B and 7-9, the shell assembly 16a of the distal tool assembly 16 includes a shell 62, the pusher 50, a cylindrical knife 64, and a staple guide 66. The shell 62 is secured to a distal end portion of the elongated body 14 and includes an outer housing portion 62a and an inner guide portion 62b.

The pusher 50 of the shell assembly 16a is slidably positioned about the inner guide portion 62b of the shell 62 and defines a central throughbore 50a. The proximal end portion of the pusher 50 includes arms 50b, 50c that are configured to lockingly engage with the fingers 40b, 40c of the pusher link 40 to fasten the pusher link 40 to the pusher 50. The distal end portion of the pusher 50 includes annular arrays of distally extending fingers 68 that are configured to be slidably received within corresponding annular arrays of slots 70 formed through a tissue contact surface 66a of the staple guide 66. In embodiments, the tissue contact surface 66a of the staple guide 66 slopes downwardly as the tissue contact surface 66a extends radially outward. The fingers 68 of the pusher 50 support an array of staples 72 that are positioned within the annular arrays of slots 70 of the staple guide 66. The annular arrays of distally extending fingers 68 include an outer array 68a of fingers 68, a middle array 68b of fingers 68, and an inner array 68c of fingers 68 that are arranged radially outward from the inner array 68c to the outer array 68a with the middle array 68b disposed between the inner and outer arrays 68c, 68a. In embodiments, the annular arrays 68a-68c of the distally extending fingers 68 are positioned in descending height order in a radial outward direction from the inner array 68c to the outer array 68a such that the inner array 68c has the largest height and the outer array 68a has the smallest height.

The annular arrays of slots 70 of the staple guide 66 of the shell assembly 16a include outer, middle, and inner arrays of slots 70a, 70b, 70c that are also arranged radially outward from the inner array 70c to the outer array 70a, and that are configured to house respective outer, middle, and inner annular arrays of staples 72a, 72b, 72c.

Also arranged radially outward from the inner array to the outer array, the respective outer, middle, and inner annular arrays of staples 72a, 72b, 72c are configured to correspond to the respective outer, middle and inner arrays of the annular arrays of slots 70 and the annular arrays of fingers 68. Although the staples may have any suitable length and/or dimension, the staples of the inner annular array of staples 72c may have 3.0 mm lengths, the staples of the middle annular array of staples 72b may have 4.0 mm lengths, and the staples of the outer annular array of staples 72a may have 5.0 mm lengths.

The cylindrical knife 64 of the shell assembly 16a is frictionally retained within the central throughbore 50a of the pusher 50 of the shell assembly 16a to fixedly secure the knife 64 in relation to the pusher 50. The distal end portion of the knife 64 includes a circular cutting edge 64a.

In operation, when the pusher link 40 of the central body portion 14 is advanced distally in response to actuation of the firing trigger 20 of the handle assembly 12, the pusher 50 of the shell assembly 16a is advanced distally within the shell 62 of the shell assembly 16a. Advancement of the pusher 50 advances the fingers 68 of the pusher 50 through the respective slots 70 of the staple guide 66 to eject the staples 72 positioned within the slots 70 from the staple guide 66. Since the knife 64 of the shell assembly 16a is secured to the pusher 50, the knife 64 is also advanced distally to core tissue positioned radially inward of the knife 64 within the shell 62.

Anvil Assembly

Figure 2A:
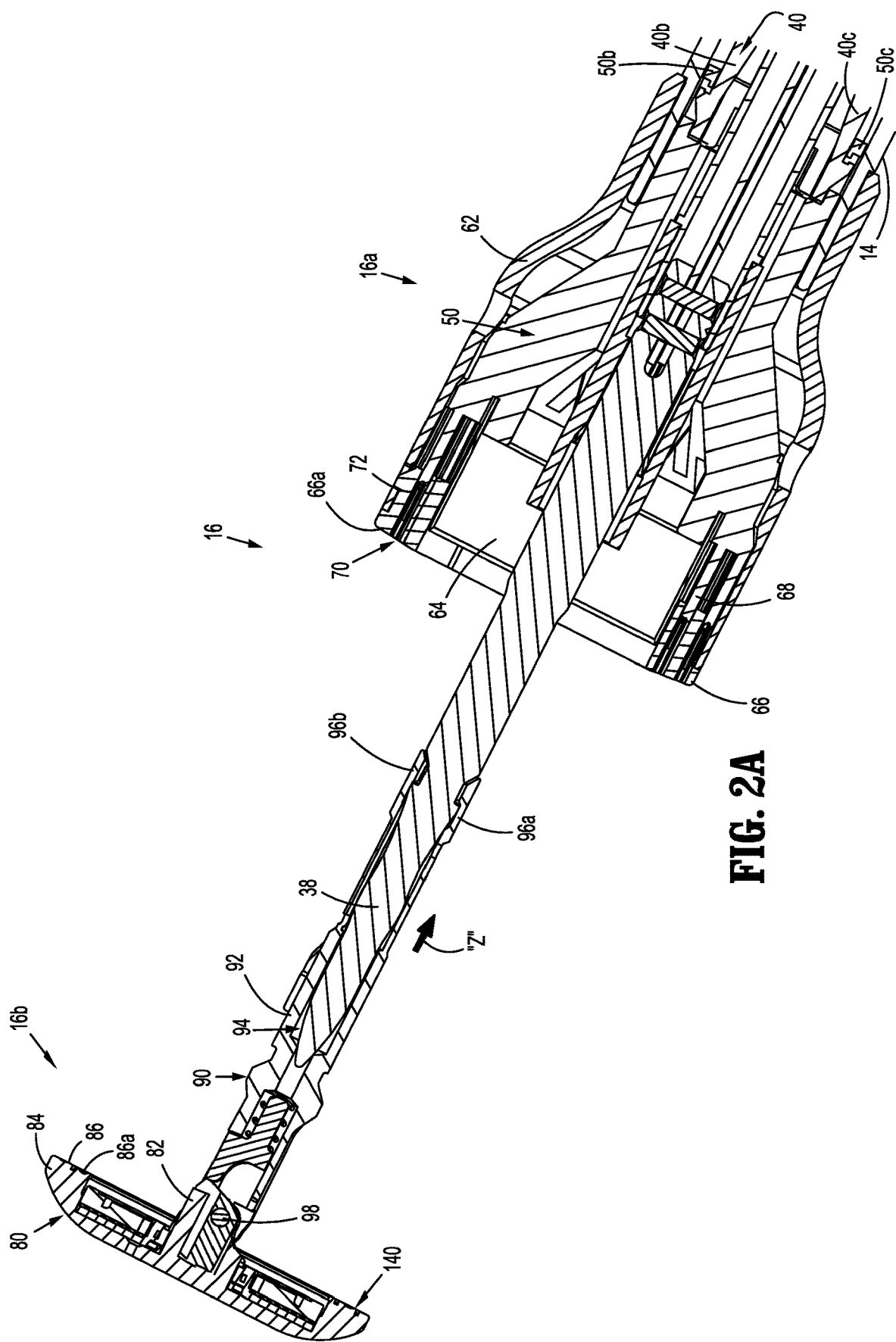
FIG. 2A is an enlarged view of the indicated area of detail shown in FIG. 2 illustrating a tool assembly of the surgical stapling device of FIG. 1 in an unapproximated position.

With reference to FIG. 2A, the anvil assembly 16b of the distal tool assembly 16 includes an anvil head assembly 80 and an anvil center rod assembly 90. The anvil head assembly 80 of the anvil assembly 16b includes a post 82, an anvil head 84, and an anvil 86. The anvil 86 is supported on the anvil head 84 of the anvil head assembly 80 and includes a tissue contact surface 86a that defines three annular arrays of pockets 140 arranged to correspond to the annular arrays of slots 70 formed in the staple guide 66. The annular arrays of pockets 140 of the anvil 86 are arranged to receive and deform the staples 72 when that staples 72 are ejected from the slots 70 of the staple guide 66. The anvil center rod assembly 90 of the anvil assembly 16b includes an anvil center rod 92 that defines a bore 94 and has flexible arms 96a, 96b. The anvil retainer 38 is received within the central bore 94 of the anvil center rod 92 such that the flexible arms 96a, 96b of the anvil center rod 92 releasably engage the anvil retainer 38 and couple the anvil retainer 38 to the center rod 92. A pivot member 98 secures the post 82 of the anvil head assembly 80 to the center rod 92 of the anvil center rod assembly 90 such that the anvil head assembly 80 is pivotably mounted to the anvil center rod assembly 90, for example, to achieve anvil tilt in which the anvil head assembly 80 is tilted relative to the anvil center rod assembly 90. Anvil tilt provides a reduced anvil profile and simplifies removal of the surgical stapling device after an anastomosis procedure has been performed. For a more detailed description of anvil tilt, reference can be made to, for example, U.S. Pat. Nos. 6,945,444, 9,307,994, and 9,492,168, the entire contents of each of which are incorporated by reference above.

Firing

Referring to FIGS. 2 and 3, when the anvil assembly 16b and the shell assembly 16a of the distal tool assembly 16 are fully approximated (FIG. 2B) and the trigger lock 24 is pivoted away from the firing trigger 20 of the handle assembly 12, the firing trigger 20 may be actuated. Actuation of the firing trigger 20 causes the firing trigger 20 to pivot about the pivot member 42 to move the firing link 44 proximally until the pivot member 48 engages the first abutment surface 58a (FIG. 13) of the screw stop 58. Continued pivoting movement of the firing trigger 20 causes the firing link 44 to push against the first abutment surface 58a of the screw stop 58 and to drive or advance the distal portion 20b of the firing trigger 20 distally. As the distal portion 20b of the firing trigger 20 advances distally, the pusher link 40 is advanced distally against the bias of (e.g., tension in) the spring 52. Distal movement or advancement of the pusher link 40 drives the pusher 50 of the shell assembly 16a distally within the staple guide 66 of the shell assembly 16a so that the fingers 68 of the pusher 50 eject the staples 72 from the slots 70 of the staple guide 66.

Audible Indicator Mechanism

With reference to FIGS. 3-6, the audible indicator mechanism 100 of the handle assembly 12 includes a mounting assembly 102, a spring assembly 104 supported by the mounting assembly 104, a support bracket 106 mounted to the mounting assembly 102, and a cam member 108 coupled to the spring assembly 104 and movably supported between the support bracket 106 and the mounting assembly 102.

The mounting assembly 102 of the audible indicator mechanism 100 includes a mounting body 110 formed in the handle assembly 12 having a plurality of mounting stems 110a. The mounting body 110 defines a cam channel 112 in a proximal portion of the mounting body 110 and an elongated channel 114 in a distal portion of the mounting body 110. The cam channel 112 includes a first leg 112a, a second leg 112b, and a third leg 112c. The first leg 112a is coupled to the second leg 112b by a first cam surface 112d. The second leg 112b is coupled to the third leg 112c by a second cam surface 112e. The third leg 112c is coupled to the first leg 112a by a third cam surface 112f.

The spring assembly 104 of the audible indicator mechanism 100 includes a spring 116 having a proximal end portion 116a and a distal end portion 116b. The proximal end portion 116a of the spring 116a is coupled to a support pin 118 that is secured to the support bracket 106 and extends laterally from the spring 116. The distal end portion 116b of the spring 116 is in the form of a hook or loop.

Figure 6:
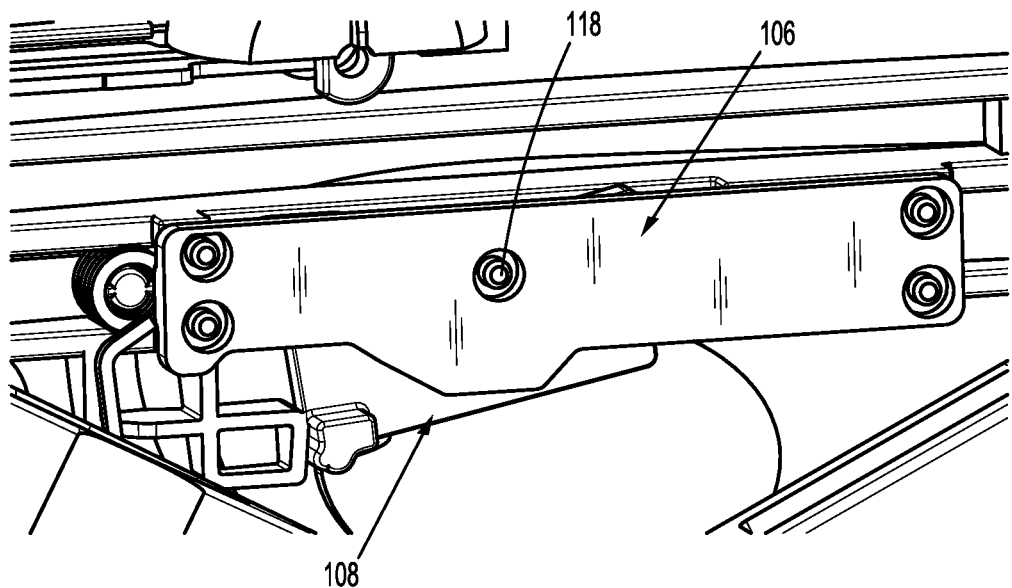
FIG. 6 is a perspective view illustrating a portion of the handle assembly shown in FIG. 3 showing a second side of the audible indicator mechanism of FIG. 4.
Figure 7:
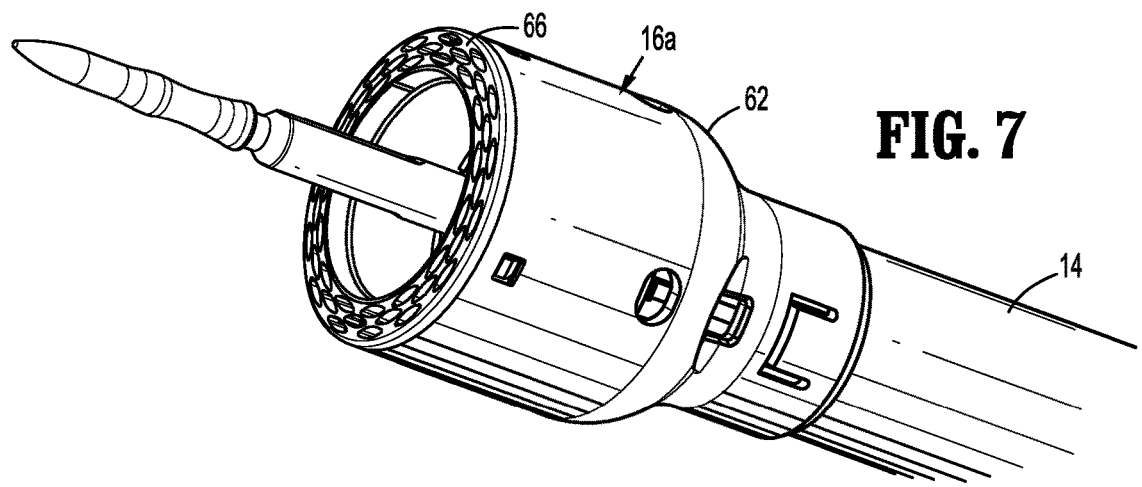
FIG. 7 is a perspective view showing a shell assembly of the surgical stapling device of FIG. 1 supported on a distal portion of an elongated central body portion of the surgical stapling device.
Figure 8:
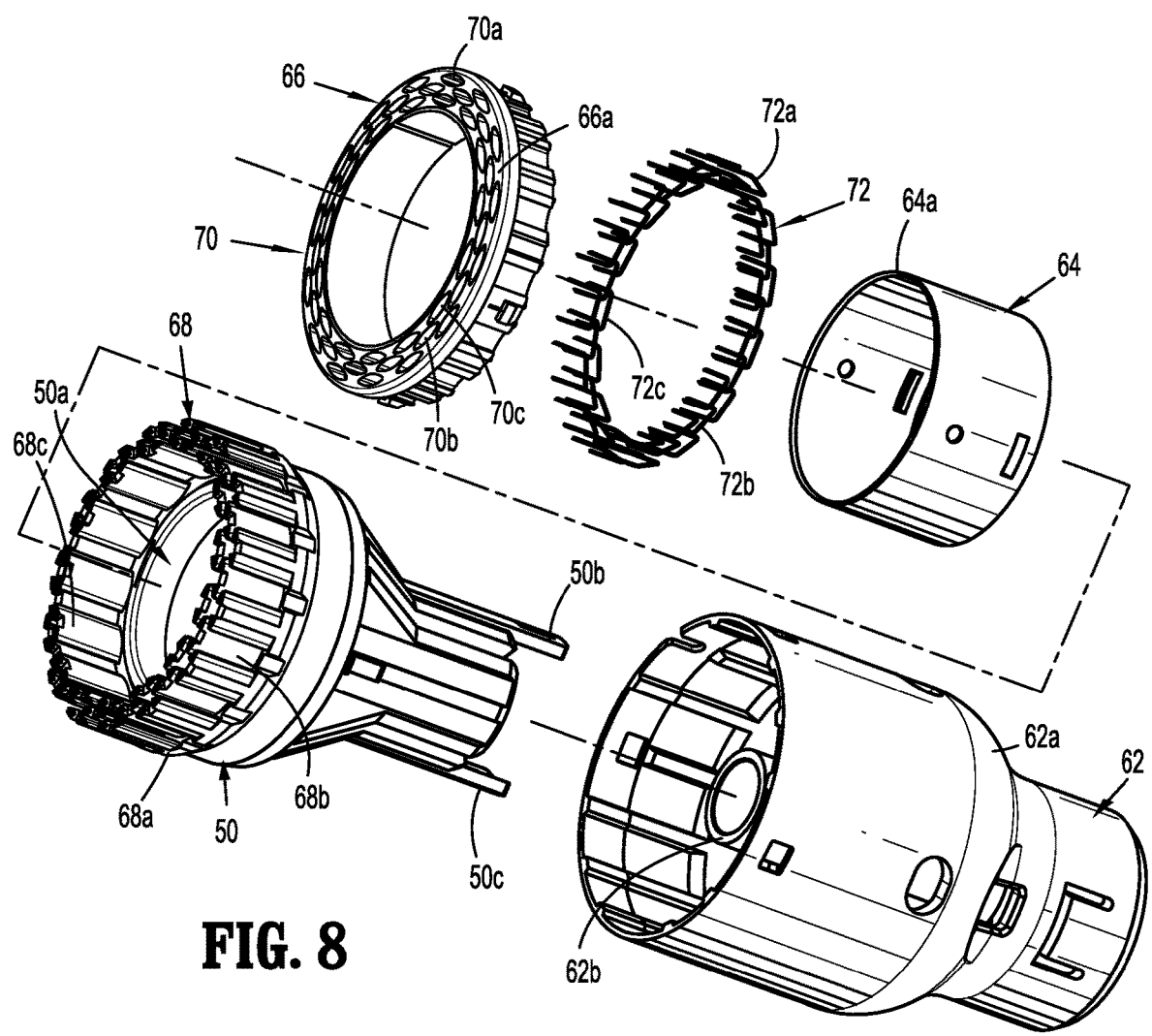
FIG. 8 is a perspective view, with parts separated, of the shell assembly of FIG. 7.
Figure 8A:
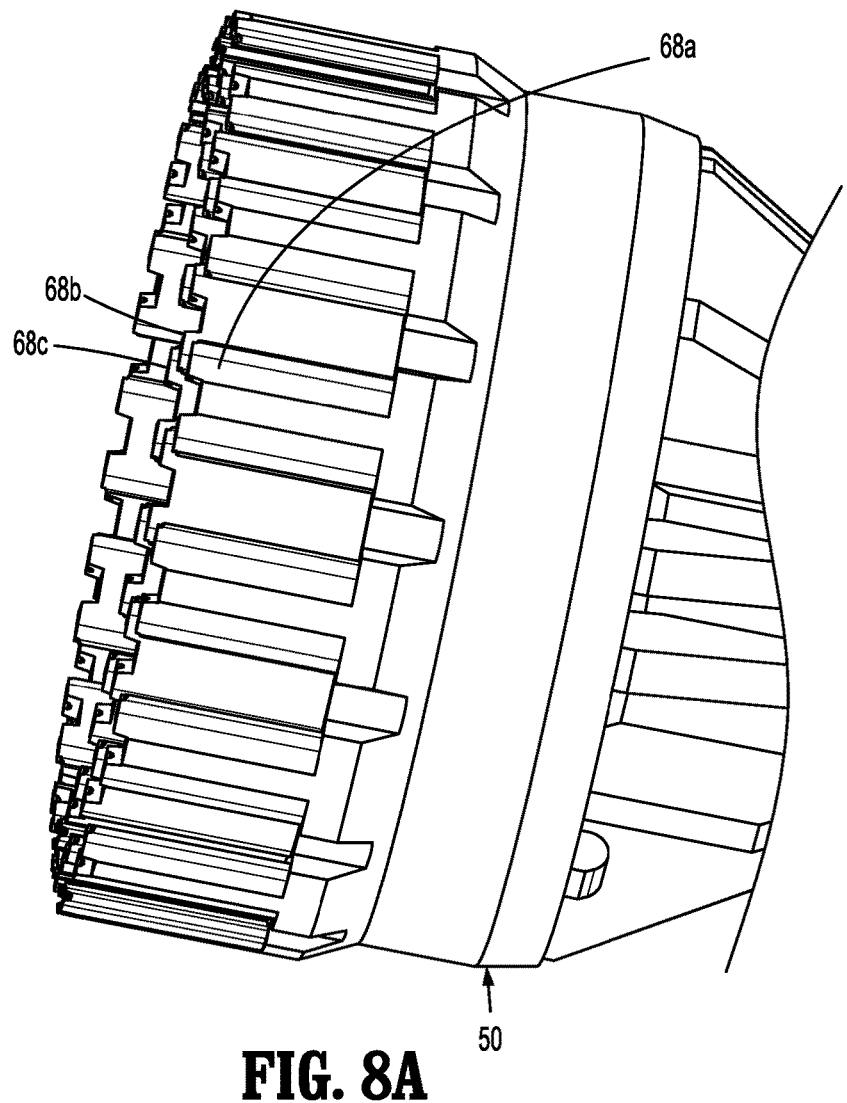
FIG. 8A is an enlarged perspective view of a distal portion of a pusher of the shell assembly of FIG. 8.
Figure 9:
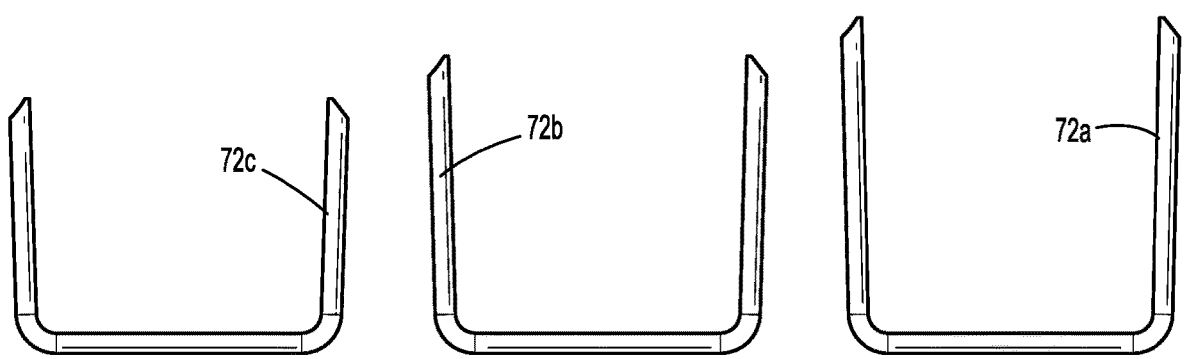
FIG. 9 is a front view of a staple from each of inner, middle, and outer rows of staples of the shell assembly of FIG. 8.

The support bracket 106 of the audible indicator mechanism 100 defines a plurality of openings 120 positioned to receive the mounting stems 110a of the mounting assembly 102 (FIG. 6). Each opening 120 of the plurality of openings 120 receives a fastener (not shown) that secures the support bracket 106 to the mounting stems 110a of the mounting assembly 102. The support bracket 106 further defines an aperture 122 that receives the support pin 118 to secure the spring assembly 104 to the support bracket 106.

The cam member 108 of the audible indicator mechanism 100 defines a central channel 124 having a proximal portion 124a and a distal portion 124b. The cam member 108 includes a cam fin 126 that extends proximally from the cam member 108. The cam member 108 further includes a cam pin 128 that extends laterally from a proximal portion of the cam member 108 and is slidably positioned in the cam channel 112 of the mounting body 110 between extended and retracted positions. The cam member 108 also includes an elbow 130 (FIG. 3) that extends laterally from a distal portion of the cam member 108 and couples to the distal end portion 116b of the spring 116.

Figure 10:
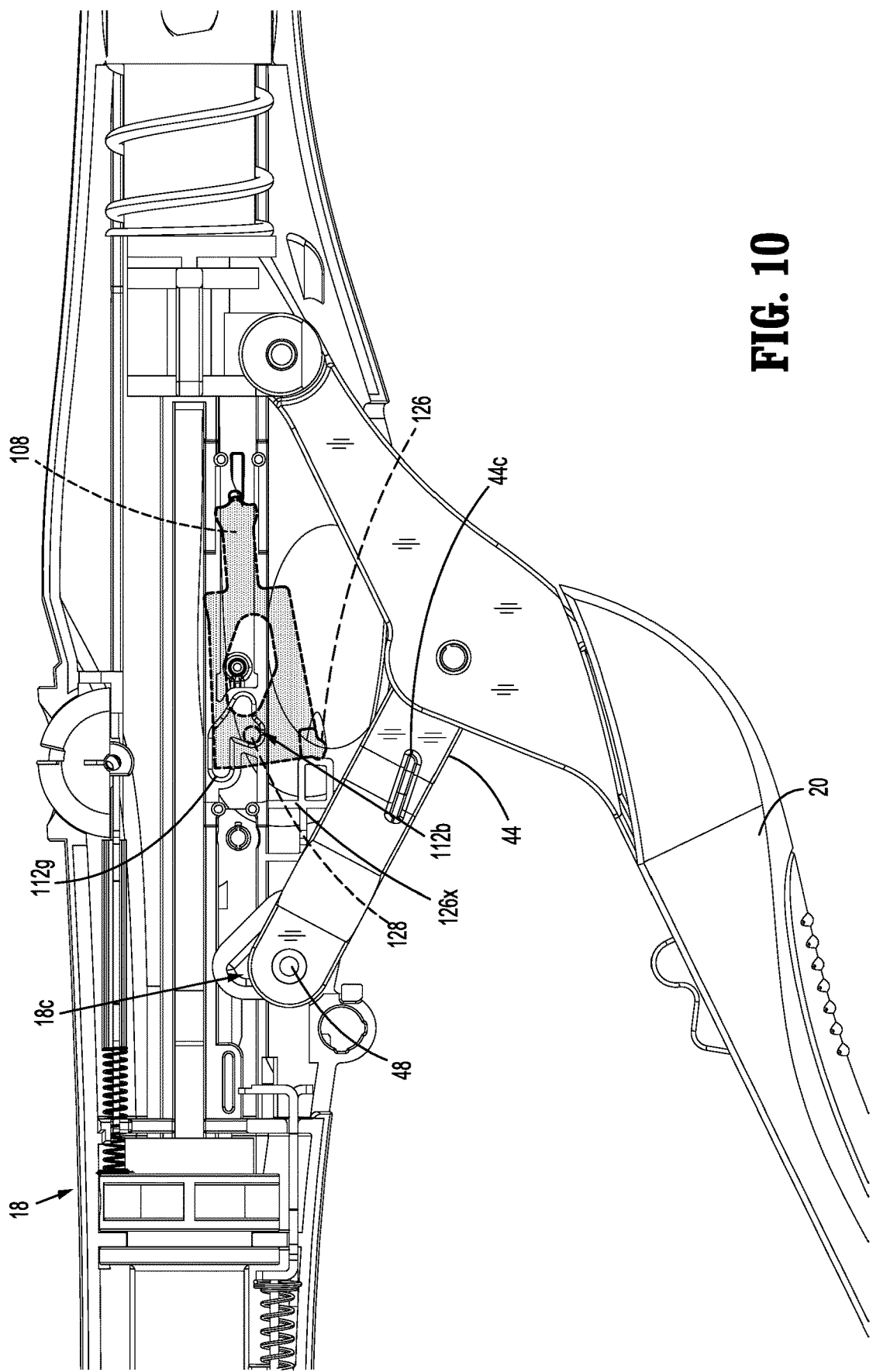
FIGS. 10-12 are progressive views illustrating operation of the audible indicator mechanism of FIG. 4 as the surgical stapling device of FIG. 1 is fired.
Figure 11:
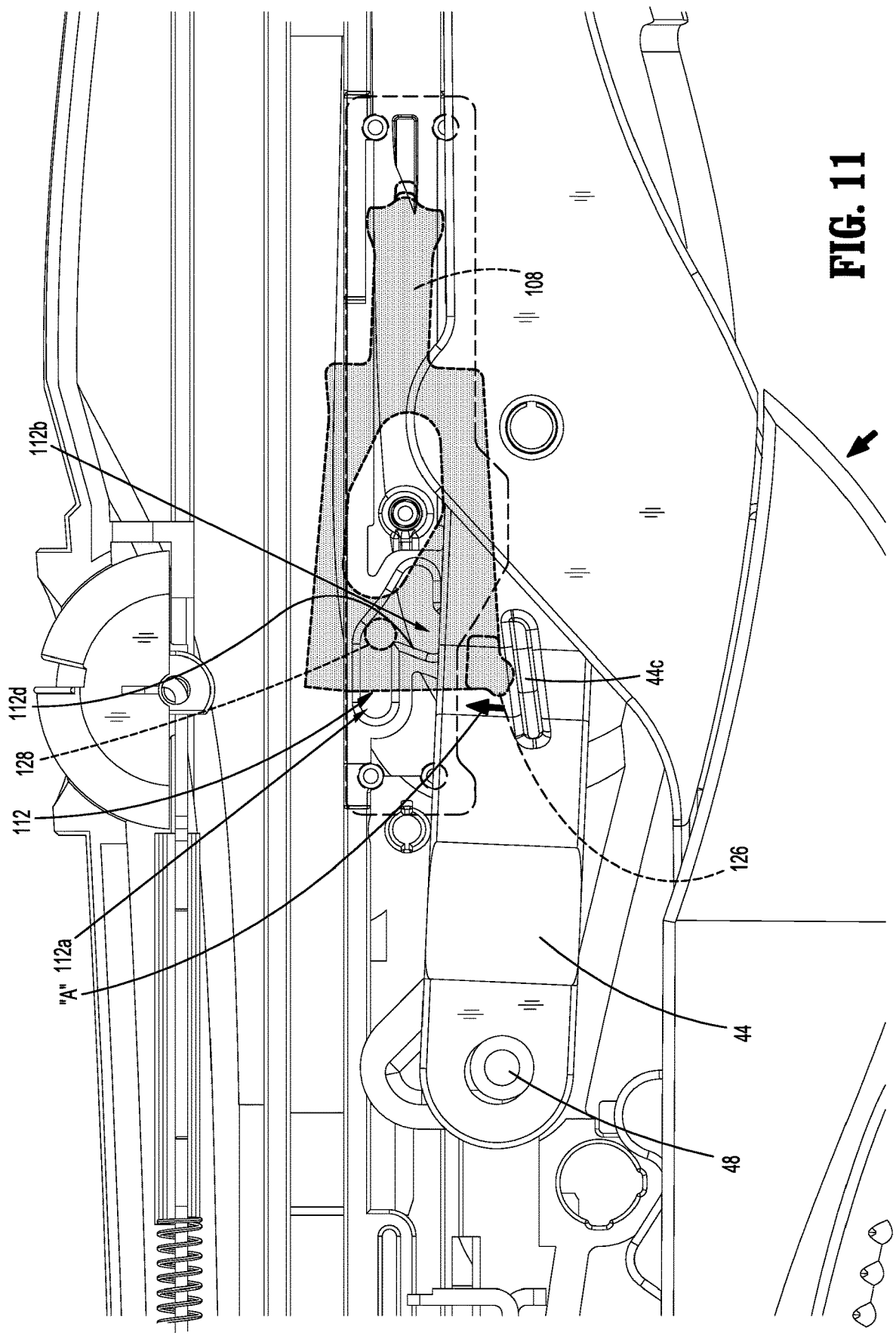
Figure 12:
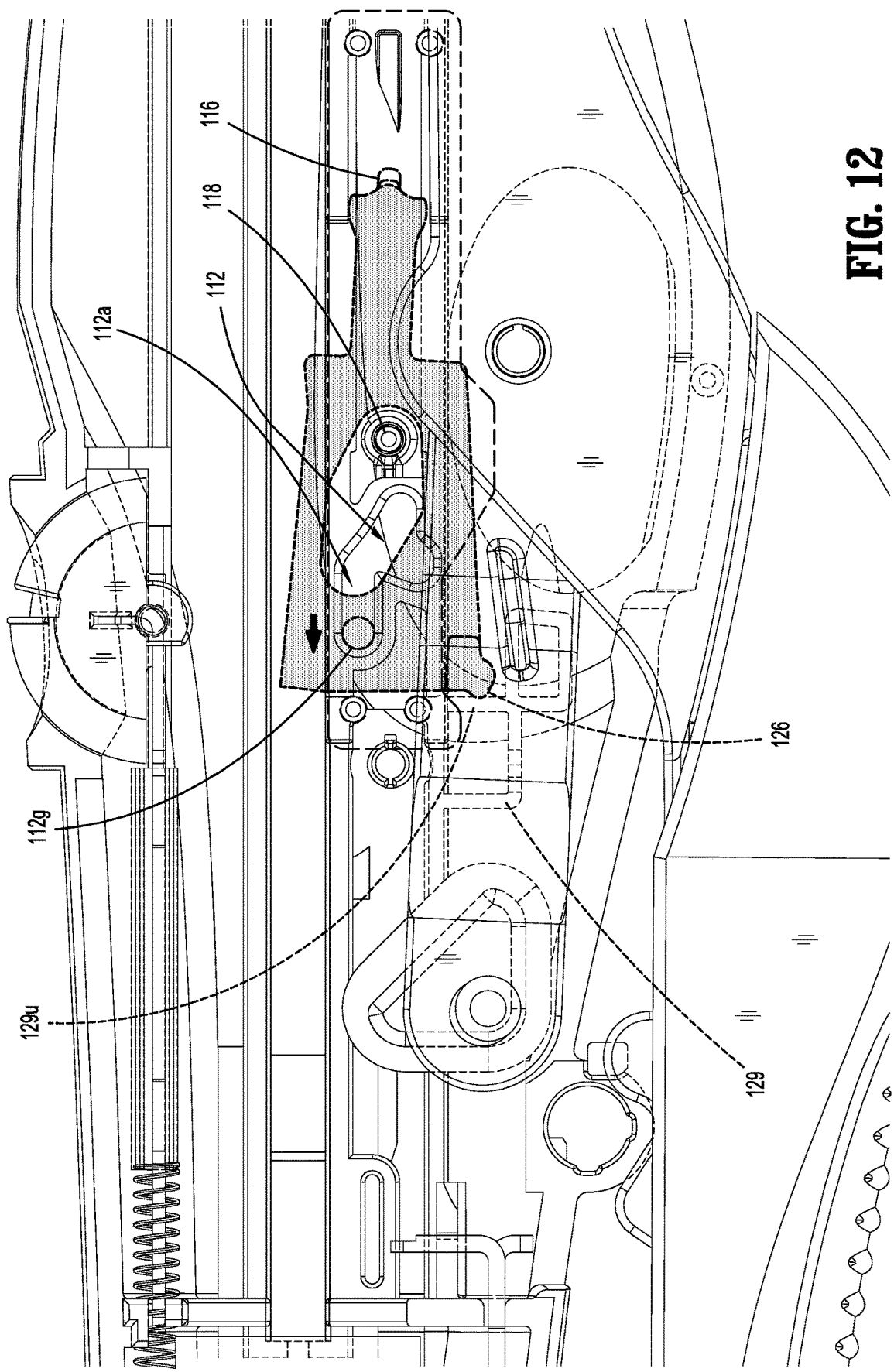

As seen in FIGS. 10-12, actuation of the firing trigger 20 of the handle assembly 12 pivots the firing link 44 in the direction indicated by arrow "A" in FIG. 11 toward the cam member 108 of the audible indicator mechanism 100 so that the wing member 44c of the firing link 44 moves toward the cam fin 126 of the cam member 108. Continued pivotal movement of the firing link 44 causes the wing member 44c to engage the cam fin 126 and drive the cam fin 126 upwardly, as indicated by arrow "A" (FIG. 11). As the cam fin 126 is driven upwardly, the cam pin 128 is driven upwardly from the second leg 112b of the cam channel 112 and distally along the first cam surface 112d of the cam channel 112. The distal movement of the cam pin 128 drives the cam member 108 distally such that the elbow 130 extends the spring 116 distally relative to the support pin 118 to tension the spring 116.

With reference to FIGS. 11 and 12, when the cam pin 128 passes over the first cam surface 112d of the cam channel 112 upon further actuation of the firing trigger 20, the spring 116 biases the cam member 108 proximally to create increased tension in the spring 116 such that the cam pin 128 snaps into the first leg 112a of the cam channel 112 and approaches a first proximal inner wall 112g of the cam member 108. As the cam pin 128 snaps into the first leg 112a of the cam channel 112, the cam fin 126 contacts a contact arm 129 of handle assembly 12 at an upper segment 129U of the contact arm 129 to provide an audible sound (e.g., a click). The audible sound indicates that firing of the surgical stapling device 10 is complete. The contact arm 129 and/or the cam fin 126, or portions thereof, can include any suitable ceramic, metallic, and/or polymeric material to enhance the sound produced by the resulting contact between the cam fin 126 and the contact arm 129 such that the sound is audibly perceptible by humans (e.g., within the frequency range of about 20 Hz to about 20 kHz).

With reference to FIGS. 13-16, once firing of the surgical stapling device 10 is complete, the knob 22 of the approximation mechanism can be rotated to unapproximate the anvil and shell assemblies 30, 31 such that the screw stop 58 is advanced distally. Distal movement of the screw stop 58 causes the wing 60*a* of the body 60 of the screw stop 58 to engage the cam member 108 such that the second abutment surface 58*b* of the wing 60*a* is in contact with a proximal surface 108*a* of the cam member 108. Continued distal advancement of the screw stop 58, as indicated by arrow "B" (FIG. 14) drives the cam member 108 distally so that the elbow 130 extends the spring 116 distally relative to the support pin 118 to increase tension in the spring 116. As the cam member 108 moves distally, the cam pin 128 moves distally out of the first leg 112*a* of the cam channel 112, as indicated by arrow "C" (FIG. 14), moves distally and downwardly along the third cam surface 112*f*, as indicated by arrow "D" (FIG. 15), into the third leg 112 of the cam channel 112 so that the wing 60*a* of the body 60 of the screw stop 58 disengages from the cam member 108. With the cam member 108 disengaged from the screw stop 58, the cam member 108 is biased proximally by the spring 116 so that the cam pin 128 moves proximally and downwardly along the second cam surface 112*e*, as indicated by arrow "E" (FIG. 16) and snaps back into the first leg 112*a* of the cam channel 112. As the cam pin 128 snaps back into the first leg 112*a* of the cam channel 112, the cam fin 126 contacts the contact arm 129 of the handle assembly 12 at a lower segment 129L of the contact arm 129 as the cam pin 128 approaches a second proximal inner wall 112*h* of the cam channel 112 to provide another audible sound (e.g., a click) that indicates anvil tilt and that the audible indicator mechanism 100 was reset. The audible sounds may be different (e.g., volume, type of sound, duration, etc., or combinations thereof, for example, due to differences in materials, dimensions of materials, and/or positional acoustics of portions of the contact arm 129 as it relates to its relative positioning within the handle assembly 12), and in some embodiments, may be the same.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A surgical stapling device, comprising:
   a proximal handle assembly including a contact arm;
   an elongated central body portion that extends distally from the proximal handle assembly to a distal end portion;
   a tool assembly supported on the distal end portion of the elongated central body portion;
   and
   an audible indicator mechanism supported by the proximal handle assembly and including a cam member, the cam member configured to contact the contact arm of the proximal handle assembly as the cam member moves between distal and proximal positions to generate an audible sound that indicates that the tool assembly was fired, the audible indicator mechanism including a mounting body defining a cam channel, the cam member including a cam pin that is slidably positioned within the cam channel to enable the cam member to move between the proximal and distal positions, the cam channel including a plurality of legs, the cam pin receivable within each leg of the plurality of legs as the cam member moves between the proximal and distal positions.

2. The surgical stapling device of claim 1, wherein the cam member includes a cam fin that is positioned to contact the contact arm of the proximal handle assembly to generate the audible sound.

3. The surgical stapling device of claim 2, wherein the contact arm includes an upper segment and a lower segment, the cam fin configured to contact one of the upper and lower segments to indicate that the tool assembly was fired.

4. The surgical stapling device of claim 1, wherein the mounting body defines an elongated channel that supports a spring, the spring coupled to a support bracket by a support pin.

5. The surgical stapling device of claim 4, wherein the spring is a compression spring that urges the cam member into contact with the contact arm in response to tension in the compression spring.

6. The surgical stapling device of claim 4, wherein the cam member defines a central channel through which the support pin extends to enable the cam member to move vertically and axially relative to the support pin as the cam member moves between the proximal and distal positions.

7. The surgical stapling device of claim 1, wherein the tool assembly includes a circular anvil and a circular shell assembly that are positioned to move between unapproximated and approximated positions.

8. The surgical stapling device of claim 1, wherein the cam member is positioned to move from the distal position to the proximal position to generate the audible sound.

9. A surgical stapling device, comprising:
   a proximal handle assembly including a contact arm;
   an elongated central body portion that extends distally from the proximal handle assembly to a distal end portion;
   a tool assembly supported on the distal end portion of the elongated central body portion;
   and
   an audible indicator mechanism supported by the proximal handle assembly and including a cam member, the cam member configured to contact the contact arm of the proximal handle assembly as the cam member moves between distal and proximal positions to generate an audible sound that indicates that the tool assembly was fired, the audible indicator mechanism including a mounting body defining a cam channel, the cam member including a cam pin that is slidably positioned within the cam channel to enable the cam member to move between the proximal and distal positions, the mounting body supporting a spring that is coupled to the cam member by an elbow extending from the cam member.

10. An audible indicator mechanism for a surgical stapling device, the audible indicator mechanism comprising:
a mounting assembly including a mounting body that defines a cam channel and an elongated channel;
a spring assembly supported by the mounting assembly, the spring assembly including a spring supported by the elongated channel of the mounting body;
a support bracket mounted to the mounting assembly;
a support pin that couples the spring to the support bracket; and
a cam member coupled to the spring assembly and supported between the support bracket and the mounting assembly, the cam member supported for movement between distal and proximal positions relative to the support bracket to generate an audible sound that indicates that the surgical stapling device was fired, the cam member including a cam pin that is slidably positioned within the cam channel to enable the cam member to move between the proximal and distal positions, wherein the cam member defines a central channel through which the support pin extends to enable the cam member to move vertically and axially relative to the support pin as the cam member moves between the proximal and distal positions.

11. The audible indicator mechanism of claim 10, wherein the cam member includes a cam fin that is positioned to generate the audible sound as the cam member moves from the distal position to the proximal position.

12. The audible indicator mechanism of claim 10, wherein the cam channel includes a plurality of legs, the cam pin receivable within each leg of the plurality of legs as the cam member moves between the proximal and distal positions.

13. The audible indicator mechanism of claim 10, wherein the spring is a compression spring that urges the cam member toward the proximal position in response to tension in the compression spring.

14. The audible indicator mechanism of claim 10, wherein the spring is coupled to the cam member by an elbow that extends from the cam member.

15. The audible indicator mechanism of claim 10, wherein the cam member is positioned to move from the distal position to the proximal position to generate the audible sound.

* * * * *